United States Patent
Stigall et al.

(10) Patent No.: US 11,141,131 B2
(45) Date of Patent: Oct. 12, 2021

(54) SMOOTH TRANSITION CATHETERS

(71) Applicant: PHILIPS IMAGE GUIDED THERAPY CORPORATION, San Diego, CA (US)

(72) Inventors: Jeremy Stigall, Carlsbad, CA (US); Maritess Minas, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 16/825,894

(22) Filed: Mar. 20, 2020

(65) Prior Publication Data
US 2020/0214665 A1    Jul. 9, 2020

Related U.S. Application Data

(63) Continuation of application No. 14/108,609, filed on Dec. 27, 2013, now Pat. No. 10,595,820.

(60) Provisional application No. 61/739,855, filed on Dec. 20, 2012.

(51) Int. Cl.
*A61B 8/12* (2006.01)
*A61B 5/00* (2006.01)
*A61M 25/01* (2006.01)

(52) U.S. Cl.
CPC .............. *A61B 8/12* (2013.01); *A61B 5/0084* (2013.01); *A61M 25/01* (2013.01); *A61M 2025/0183* (2013.01)

(58) Field of Classification Search
None
See application file for complete search history.

(56) References Cited

U.S. PATENT DOCUMENTS

| | | | |
|---|---|---|---|
| 3,301,258 A | 1/1967 | Werner | |
| 3,617,880 A | 11/1971 | Cormack et al. | |
| 3,789,841 A | 2/1974 | Antoshkiw | |
| 3,841,308 A | 10/1974 | Tate | |
| 3,989,571 A * | 11/1976 | Harautuneian | A61M 16/04 156/250 |
| 4,140,364 A | 2/1979 | Yamashita et al. | |

(Continued)

FOREIGN PATENT DOCUMENTS

| EP | 1041373 A2 | 10/2000 |
|---|---|---|
| EP | 01172637 A1 | 1/2002 |

(Continued)

OTHER PUBLICATIONS

Li et al., 2000, Optical Coherence Tomography: Advanced Technology for the Endoscopic Imaging of Barrett's Esophagus, Endoscopy, 32(12):921-930.

(Continued)

*Primary Examiner* — Pascal M Bui Pho
*Assistant Examiner* — Marjan Saboktakin

(57) ABSTRACT

The present invention generally relates to a rapid exchange configuration that reduces the profile of a catheter riding on a guidewire and minimizes guidewire resistance. According to certain embodiments, a body of the catheter includes a distal portion and a proximal portion. The distal portion defines a guidewire lumen and includes a guidewire exit port being open in an proximal direction and leading to the guidewire lumen. A proximal section of the guidewire lumen is straight.

12 Claims, 9 Drawing Sheets

(56) References Cited

U.S. PATENT DOCUMENTS

| | | |
|---|---|---|
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,766,386 A | 5/1988 | Oliver et al. |
| 4,762,129 A | 8/1988 | Bonzel |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,617 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,300,025 A | 4/1994 | Wantink |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,520,647 A | 5/1996 | Solar |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,569,215 A | 10/1996 | Crocker |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |

(56) References Cited

U.S. PATENT DOCUMENTS

| | | |
|---|---|---|
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,004,291 A | 12/1999 | Ressemann |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,193,686 B1 | 2/2001 | Estrada |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,409,863 B1 | 6/2002 | Williams |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Guiachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B2 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |

(56) References Cited

U.S. PATENT DOCUMENTS

| | | | |
|---|---|---|---|
| 6,673,064 B1 | 1/2004 | Rentrop | |
| 6,685,648 B2 | 2/2004 | Flaherty et al. | |
| 6,689,056 B1 | 2/2004 | Kilcoyne et al. | |
| 6,689,144 B2 | 2/2004 | Gerberding | |
| 6,696,173 B1 | 2/2004 | Naundorf et al. | |
| 6,701,044 B2 | 3/2004 | Arbore et al. | |
| 6,701,176 B1 | 3/2004 | Halperin et al. | |
| 6,709,444 B1 | 3/2004 | Makower | |
| 6,712,836 B1 | 3/2004 | Berg et al. | |
| 6,714,703 B2 | 3/2004 | Lee et al. | |
| 6,719,717 B1 | 4/2004 | Johnson et al. | |
| 6,725,073 B1 | 4/2004 | Motamedi et al. | |
| 6,726,677 B1 | 4/2004 | Flaherty et al. | |
| 6,730,107 B2 | 5/2004 | Kelley et al. | |
| 6,733,474 B2 | 5/2004 | Kusleika | |
| 6,738,144 B1 | 5/2004 | Dogariu | |
| 6,740,113 B2 | 5/2004 | Vrba | |
| 6,746,464 B1 | 6/2004 | Makower | |
| 6,780,157 B2 | 8/2004 | Stephens et al. | |
| 6,795,188 B2 | 9/2004 | Ruck et al. | |
| 6,795,196 B2 | 9/2004 | Funakawa | |
| 6,798,522 B2 | 9/2004 | Stolte et al. | |
| 6,822,798 B2 | 11/2004 | Wu et al. | |
| 6,830,559 B2 | 12/2004 | Schock | |
| 6,832,024 B2 | 12/2004 | Gerstenberger et al. | |
| 6,842,639 B1 | 1/2005 | Winston et al. | |
| 6,847,449 B2 | 1/2005 | Bashkansky et al. | |
| 6,855,115 B2 | 2/2005 | Fonseca et al. | |
| 6,856,138 B2 | 2/2005 | Bohley | |
| 6,856,400 B1 | 2/2005 | Froggatt | |
| 6,856,472 B2 | 2/2005 | Herman et al. | |
| 6,860,867 B2 | 3/2005 | Seward et al. | |
| 6,866,670 B2 | 3/2005 | Rabiner et al. | |
| 6,878,113 B2 | 4/2005 | Miwa et al. | |
| 6,886,411 B2 | 5/2005 | Kjellman et al. | |
| 6,891,984 B2 | 5/2005 | Petersen et al. | |
| 6,895,106 B2 | 5/2005 | Wang et al. | |
| 6,898,337 B2 | 5/2005 | Averett et al. | |
| 6,900,897 B2 | 5/2005 | Froggaft | |
| 6,912,051 B2 | 6/2005 | Jensen | |
| 6,916,329 B1 | 7/2005 | Zhao | |
| 6,922,498 B2 | 7/2005 | Shah | |
| 6,937,346 B2 | 8/2005 | Nebendahl et al. | |
| 6,937,696 B1 | 8/2005 | Mostafavi | |
| 6,943,939 B1 | 9/2005 | DiJaili et al. | |
| 6,947,147 B2 | 9/2005 | Motamedi et al. | |
| 6,947,787 B2 | 9/2005 | Webler | |
| 6,949,094 B2 | 9/2005 | Yaron | |
| 6,952,603 B2 | 10/2005 | Gerber et al. | |
| 6,954,737 B2 | 10/2005 | Kalantar et al. | |
| 6,958,042 B2 | 10/2005 | Honda | |
| 6,961,123 B1 | 11/2005 | Wang et al. | |
| 6,966,891 B2 | 11/2005 | Ookubo et al. | |
| 6,969,293 B2 | 11/2005 | Thai | |
| 6,969,395 B2 | 11/2005 | Eskuri | |
| 6,985,234 B2 | 1/2006 | Anderson | |
| 7,004,963 B2 | 2/2006 | Wang et al. | |
| 7,006,231 B2 | 2/2006 | Ostrovsky et al. | |
| 7,010,458 B2 | 3/2006 | Wilt | |
| 7,024,025 B2 | 4/2006 | Sathyanarayana | |
| 7,027,211 B1 | 4/2006 | Ruffa | |
| 7,027,743 B1 | 4/2006 | Tucker et al. | |
| 7,033,347 B2 | 4/2006 | Appling | |
| 7,035,484 B2 | 4/2006 | Silberberg et al. | |
| 7,037,269 B2 | 5/2006 | Nix et al. | |
| 7,042,573 B2 | 5/2006 | Froggatt | |
| 7,044,915 B2 | 5/2006 | White et al. | |
| 7,044,964 B2 | 5/2006 | Jang et al. | |
| 7,048,711 B2 | 5/2006 | Rosenman et al. | |
| 7,049,306 B2 | 5/2006 | Konradi et al. | |
| 7,058,239 B2 | 6/2006 | Singh et al. | |
| 7,060,033 B2 | 6/2006 | White et al. | |
| 7,060,421 B2 | 6/2006 | Naundorf et al. | |
| 7,063,679 B2 | 6/2006 | Maguire et al. | |
| 7,068,852 B2 | 6/2006 | Braica | |
| 7,074,188 B2 | 7/2006 | Nair et al. | |
| 7,095,493 B2 | 8/2006 | Harres | |
| 7,110,119 B2 | 9/2006 | Maestle | |
| 7,113,875 B2 | 9/2006 | Terashima et al. | |
| 7,123,777 B2 | 10/2006 | Rondinelli et al. | |
| 7,130,054 B2 | 10/2006 | Ostrovsky et al. | |
| 7,139,440 B2 | 11/2006 | Rondinelli et al. | |
| 7,153,299 B1 | 12/2006 | Tu et al. | |
| 7,171,078 B2 | 1/2007 | Sasaki et al. | |
| 7,175,597 B2 | 2/2007 | Vince et al. | |
| 7,177,491 B2 | 2/2007 | Dave et al. | |
| 7,190,464 B2 | 3/2007 | Alphonse | |
| 7,215,802 B2 | 5/2007 | Klingensmith et al. | |
| 7,218,811 B2 | 5/2007 | Shigenaga et al. | |
| 7,236,812 B1 | 6/2007 | Ballerstadt et al. | |
| 7,245,125 B2 | 7/2007 | Harer et al. | |
| 7,245,789 B2 | 7/2007 | Bates et al. | |
| 7,249,357 B2 | 7/2007 | Landman et al. | |
| 7,291,146 B2 | 11/2007 | Steinke et al. | |
| 7,292,715 B2 | 11/2007 | Furnish | |
| 7,292,885 B2 | 11/2007 | Scott et al. | |
| 7,294,124 B2 | 11/2007 | Eidenschink | |
| 7,300,460 B2 | 11/2007 | Levine et al. | |
| 7,335,161 B2 | 2/2008 | Von Arx et al. | |
| 7,337,079 B2 | 2/2008 | Park et al. | |
| 7,355,716 B2 | 4/2008 | de Boer et al. | |
| 7,356,367 B2 | 4/2008 | Liang et al. | |
| 7,358,921 B2 | 4/2008 | Snyder et al. | |
| 7,359,062 B2 | 4/2008 | Chen et al. | |
| 7,359,554 B2 | 4/2008 | Klingensmith et al. | |
| 7,363,927 B2 | 4/2008 | Ravikumar | |
| 7,366,376 B2 | 4/2008 | Shishkov et al. | |
| 7,382,949 B2 | 6/2008 | Bouma et al. | |
| 7,387,636 B2 | 6/2008 | Cohn et al. | |
| 7,391,520 B2 | 6/2008 | Zhou et al. | |
| 7,397,935 B2 | 7/2008 | Kimmel et al. | |
| 7,399,095 B2 | 7/2008 | Rondinelli | |
| 7,408,648 B2 | 8/2008 | Kleen et al. | |
| 7,414,779 B2 | 8/2008 | Huber et al. | |
| 7,440,087 B2 | 10/2008 | Froggatt et al. | |
| 7,447,388 B2 | 11/2008 | Bates et al. | |
| 7,449,821 B2 | 11/2008 | Dausch | |
| 7,450,165 B2 | 11/2008 | Ahiska | |
| RE40,608 E | 12/2008 | Glover et al. | |
| 7,458,967 B2 | 12/2008 | Appling et al. | |
| 7,463,362 B2 | 12/2008 | Lasker et al. | |
| 7,463,759 B2 | 12/2008 | Klingensmith et al. | |
| 7,491,226 B2 | 2/2009 | Palmaz et al. | |
| 7,515,276 B2 | 4/2009 | Froggatt et al. | |
| 7,527,594 B2 | 5/2009 | Vardi et al. | |
| 7,534,251 B2 | 5/2009 | WasDyke | |
| 7,535,797 B2 | 5/2009 | Peng et al. | |
| 7,547,304 B2 | 6/2009 | Johnson | |
| 7,564,949 B2 | 7/2009 | Sattler et al. | |
| 7,577,471 B2 | 8/2009 | Camus et al. | |
| 7,583,857 B2 | 9/2009 | Xu et al. | |
| 7,603,165 B2 | 10/2009 | Townsend et al. | |
| 7,612,773 B2 | 11/2009 | Magnin et al. | |
| 7,633,627 B2 | 12/2009 | Choma et al. | |
| 7,645,229 B2 | 1/2010 | Armstrong | |
| 7,658,715 B2 | 2/2010 | Park et al. | |
| 7,660,452 B2 | 2/2010 | Zwirn et al. | |
| 7,660,492 B2 | 2/2010 | Bates et al. | |
| 7,666,204 B2 | 2/2010 | Thornton et al. | |
| 7,672,790 B2 | 3/2010 | McGraw et al. | |
| 7,680,247 B2 | 3/2010 | Atzinger et al. | |
| 7,684,991 B2 | 3/2010 | Stohr et al. | |
| 7,711,413 B2 | 5/2010 | Feldman et al. | |
| 7,720,322 B2 | 5/2010 | Prisco | |
| 7,728,986 B2 | 6/2010 | Lasker et al. | |
| 7,734,009 B2 | 6/2010 | Brunner et al. | |
| 7,736,317 B2 | 6/2010 | Stephens et al. | |
| 7,742,795 B2 | 6/2010 | Stone et al. | |
| 7,743,189 B2 | 6/2010 | Brown et al. | |
| 7,762,954 B2 | 7/2010 | Nix et al. | |
| 7,766,896 B2 | 8/2010 | Kornkven Volk et al. | |
| 7,773,792 B2 | 8/2010 | Kimmel et al. | |
| 7,775,981 B1 | 8/2010 | Guracar et al. | |
| 7,777,399 B2 | 8/2010 | Eidenschink et al. | |

(56) References Cited

U.S. PATENT DOCUMENTS

| | | |
|---|---|---|
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 9,414,495 B2 | 8/2016 | Gutierrez |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |

(56) References Cited

U.S. PATENT DOCUMENTS

| | | |
|---|---|---|
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0131449 A1 | 6/2005 | Salahieh |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2005/0283221 A1 | 12/2005 | Mann |
| 2006/0013523 A1 | 1/2006 | Childers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0041246 A1* | 2/2006 | Provost-tine ..... A61M 25/0023 604/528 |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Weber et al. |
| 2006/0064074 A1 | 3/2006 | Mallaby |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0259062 A1 | 11/2006 | Konstantino |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0282270 A1 | 12/2007 | Mathews |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |

(56) References Cited

U.S. PATENT DOCUMENTS

| | | |
|---|---|---|
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0171980 A1 | 7/2008 | Hughes |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1* | 1/2009 | Dick ............... A61B 5/0066 600/109 |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0010334 A1 | 1/2010 | Bleich et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0217234 A1 | 8/2010 | Grovender |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnsen et al. |
| 2011/0087104 A1 | 4/2011 | Moore et al. |
| 2011/0137124 A1 | 6/2011 | Milner et al. |
| 2011/0137140 A1 | 6/2011 | Tearney et al. |
| 2011/0144502 A1 | 6/2011 | Zhou et al. |
| 2011/0147080 A1* | 6/2011 | Slininger ........... H01R 43/0221 174/84 R |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0245807 A1 | 10/2011 | Sakata |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |

(56) References Cited

U.S. PATENT DOCUMENTS

| | | |
|---|---|---|
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| JP | 2012223206 A | 11/2012 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/044296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/000799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/06886 A2 | 1/2011 |

(56) References Cited

FOREIGN PATENT DOCUMENTS

| | | |
|---|---|---|
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2012014860 A1 | 9/2013 |
| WO | 2014/109879 A1 | 7/2014 |

OTHER PUBLICATIONS

Little et al., 1991, The underlying coronary lesion in myocardial infarction:implications for coronary angiography, Clinical Cardiology, 14(11):868-874.

Loo, 2004, Nanoshell Enabled Photonics-Based Imaging and Therapy of Cancer, Technology in Cancer Research & Treatment 3(1):33-40.

Machine translation of JP 2000-097846.

Machine translation of JP 2000-321034.

Machine translation of JP 2000-329534.

Machine translation of JP 2004-004080.

Maintz et al., 1998, An Overview of Medcal Image Registration Methods, Technical Report UU-CS, (22 pages).

Mamas et al., 2010, Resting Pd/Pa measured with intracoronary pressure wire strongly predicts fractional flow reserve, Journal of Invasive Cardiology 22(6):260-265.

Marks et al., 1991, By-passing Immunization Human Antibodies from V-gene Libraries Displayed on Phage, J. Mol. Biol. 222:581-597.

Marks et al., 1992, By-Passing Immunization:Building High Affinity Human Antibodies by Chain Shuffling, BioTechnol., 10:779-783.

Maruno et al., 1991, Fluorine containing optical adhesives for optical communications systems, J. Appl. Polymer. Sci. 42:2141-2148.

McCafferty et al., 1990, Phage antibodies: filamentous phage displaying antibody variable domains, Nature 348:552-554.

Mendieta et al., 1996, Complementary sequence correlations with applications to reflectometry studies, Instrumentation and Development 3(6):37-46.

Mickley, 2008, Steal Syndrome-strategies to preserve vascular access and extremity, Nephrol Dial Transplant 23:19-24.

Miller et al., 2010, The MILLER banding procedure is an effective method for treating dialysis-associated steal syndrome, Kidney International 77:359-366.

Milstein et al., 1983, Hybrid hybridomas and their use in immunohistochemistry, Nature 305:537-540.

Mindlin et al., 1936, A force at a point of a semi-infinite solid, Physics, 7:195-202.

Morrison et al., 1984, Chimeric human antibody molecules: mouse antigen-binding domains with human constant region domains, PNAS 81:6851-6855.

Munson et al., 1980, Ligand: a versatile computerized approach for characterization of ligand-binding systems, Analytical Biochemistry, 107:220-239.

Nezam, 2008, High Speed Polygon-Scanner-Based Wavelength-Swept Laser Source in the Telescope-Less Configurations with Application in Optical Coherence Tomography, Optics Letters 33(15):1741-1743.

Nissen, 2001, Coronary Angiography and Intravascular Ultrasound, American Journal of Cardiology, 87 (suppl):15A-20A.

Nitenberg et al., 1995, Coronary vascular reserve in humans: a critical review of methods of evaluation and of interpretation of the results, Eur Heart J. 16(Suppl 1):7-21.

Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).

Nygren, 1982, Conjugation of horseradish peroxidase to Fab fragments with different homobifunctional and heterobifunctional cross-linking reagents. A comparative study, J. Histochem. and Cytochem. 30:407-412.

Oesterle et al., 1986, Angioplasty at coronary bifurcations: single-guide, two-wire technique, Cathet Cardiovasc Diagn., 12:57-63.

Okuno et al., 2003, Recent Advances in Optical Switches Using Silica-based PLC Technology, NTT Technical Review 1(7):20-30.

Oldenburg et al., 1998, Nanoengineering of Optical Resonances, Chemical Physics Letters 288:243-247.

Oldenburg et al., 2003, Fast-Fourier-Domain Delay Line for In Vivo Optical Coherence Tomography with a Polygonal Scanner, Applied Optics, 42(22):4606-4611.

Othonos, 1997, Fiber Bragg gratings, Review of Scientific Instruments 68(12):4309-4341.

Owens et al., 2007, A Survey of General-Purpose Computation on Graphics Hardware, Computer Graphics Forum 26(1):80-113.

Pain et al., 1981, Preparation of protein A-peroxidase mono conjugate using a heterobifunctional reagent, and its use in enzyme immunoassays, J Immunol Methods, 40:219-30.

Park et al., 2005, Real-time fiber-based multi-functional spectral-domain optical coherence tomography at 1.3 um., Optics Express 13(11):3931-3944.

Pasquesi et al., 2006, In vivo detection of exercise induced ultra-structural changes in genetically-altered murine skeletal muscle using polarization-sensitive optical coherence tomography, Optics Express 14(4):1547-1556.

Pepe et al., 2004, Limitations of the odds ratio in gauging the performance of a diagnostic, prognostic, or screening marker, American Journal of Epidemiology 159(9):882-890.

Persson et al., 1985, Acoustic impedance matching of medical ultrasound transducers, Ultrasonics, 23(2):83-89.

Placht et al., 2012, Fast time-of-flight camera based surface registration for radiotherapy patient positioning, Medical Physics 39(1):4-17.

Rabbani et al., 1999, Review: Strategies to achieve coronary arterial plaque stabilization, Cardiovascular Research 41:402-417.

Radvany et al., 2008, Plaque Excision in Management of Lower Extremity Peripheral Arterial Disease with the SilverHawk Atherectomy Catheter, Seminars in Interventional Radiology, 25(1):11-19.

Reddy et al., 1996, An FFT-Based Technique for Translation, Rotation, and Scale-Invariant Image Registration, IEEE Transaction on Image Processing 5(8):1266-1271.

Riechmann et al., 1988, Reshaping human antibodies for therapy, Nature, 332:323-327.

Rivers et al., 1992, Correction of steal syndrome secondary to hemodialysis access fistulas: a simplified quantitative technique, Surgery, 112(3):593-7.

Robbin et al., 2002, Hemodialysis Arteriovenous Fistula Maturity: US Evaluation, Radiology 225:59-64.

Rollins et al., 1998, In vivo video rate optical coherence tomography, Optics Express 3:219-229.

Sarunic et al., 2005, Instantaneous Complex Conjugate Resolved Spectral Domain and Swept-Source OCT Using 3×3 Fiber Couplers, Optics Express 13(3):957-967.

Satiani et al., 2009, Predicted Shortage of Vascular Surgeons in the United States, J. Vascular Surgery 50:946-952.

Schneider et al., 2006, T-banding: A technique for flow reduction of a hyper-functioning arteriovenous fistula, J Vasc Surg. 43(2):402-405.

(56) References Cited

OTHER PUBLICATIONS

Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
International Search Report and Written Opinion dated Nov. 2, 2012, for International Patent Application No. PCT/US12/53168, filed Aug. 30, 2013 (8 pages).
International Search Report and Written Opinion dated Apr. 14, 2014, for International Patent Application No. PCT/US2013/076148 filed Dec. 18, 2013 (8 pages).
International Search Report and Written Opinion dated Apr. 21, 2014, for International Patent Application PCT/US2013/076015, filed Dec. 18, 2013 (7 pages).
International Search Report and Written Opinion dated Apr. 23, 2014, for International Patent Application No. PCT/US2013/075328, filed Dec. 16, 2013 (8 pages).
International Search Report and Written Opinion dated Apr. 29, 2014, for International Patent Application No. PCT/US13/76093, filed Dec. 18, 2013 (6 pages).
International Search Report and Written Opinion dated Apr. 30, 2014, for International Patent Application No. PCT/US13/75641, filed Dec. 17, 2013 (17 pages).
International Search Report and Written Opinion dated Apr. 9, 2014, for International Patent Application No. PCT/US13/75089, filed Dec. 13, 2013 (7 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Jan. 16, 2009, for International Patent Application No. PCT/US08/78963 filed on Oct. 6, 2008 (7 Pages).
International Search Report and Written Opinion dated Jul. 30, 2014, for International Patent Application No. PCT/US14/21659, filed Mar. 7, 2014 (15 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US13/75349, filed Dec. 16, 2013 (10 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.

(56) References Cited

OTHER PUBLICATIONS

Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Shen et al., 2006, Eigengene-based linear discriminant model for tumor classification using gene expression microarray data, Bioinformatics 22(21):2635-2642.
Sihan et al., 2008, A novel approach to quantitative analysis of intraluminal optical coherence tomography imaging, Comput. Cardiol:1089-1092.
Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelson interferometer, Applied Optics, 28(16):3339-3342.
Smith, 1997, The Scientist and Engineers Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60 (9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells, EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12(24):6033-6039.
Zitova et al., 2003, Image registration methods: A survey. Image and Vision Computing, 21(11):977-1000.
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode—Locked Lasers, Optics Letters, 32(6):626-628.
Agresti, 1996, Models for Matched Pairs, Chapter 8, an Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.

(56) References Cited

OTHER PUBLICATIONS

Bail et al., 1996, Optical coherence tomography with the "Spectral Radar"-Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring-the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.

Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radiofrequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075353, filed Dec. 16, 2013 (8 pages).

* cited by examiner (Prior Art)
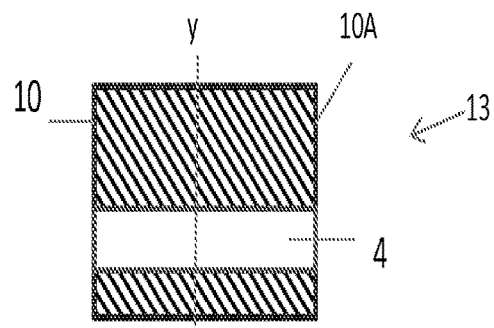
FIG. 2A
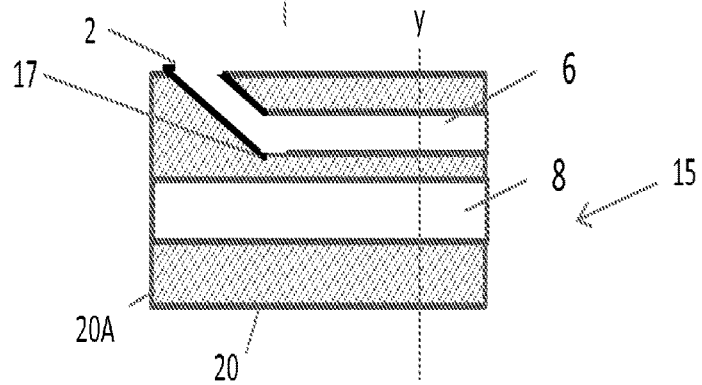
FIG. 2B
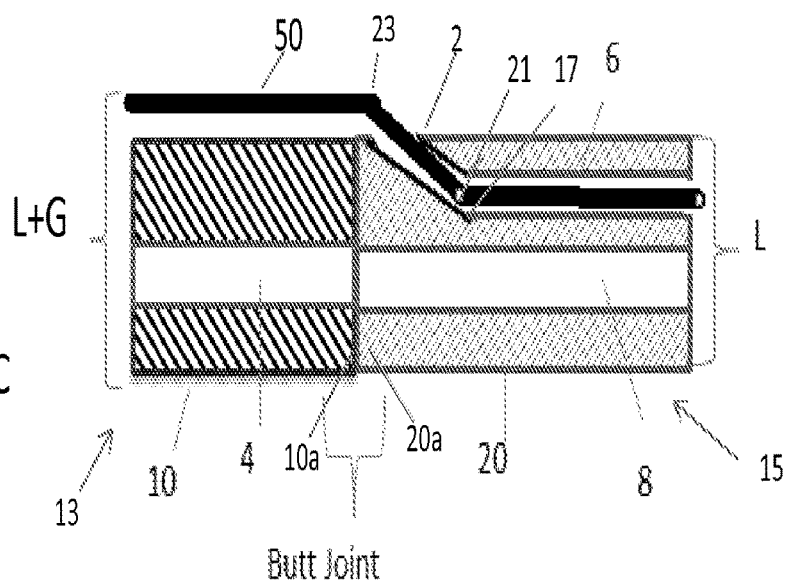
FIG. 2C
Butt Joint
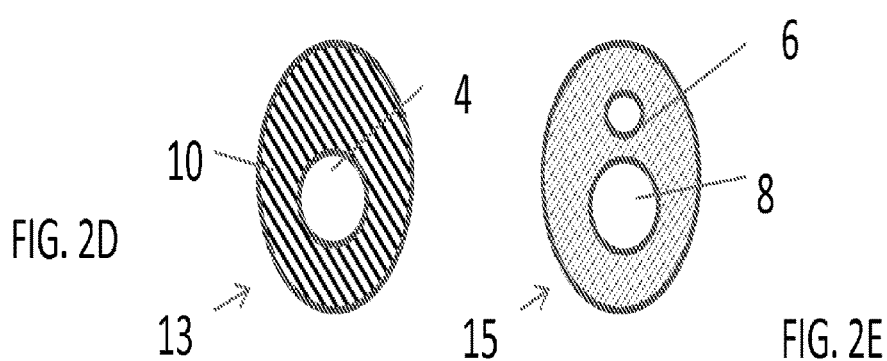
FIG. 2D
FIG. 2E

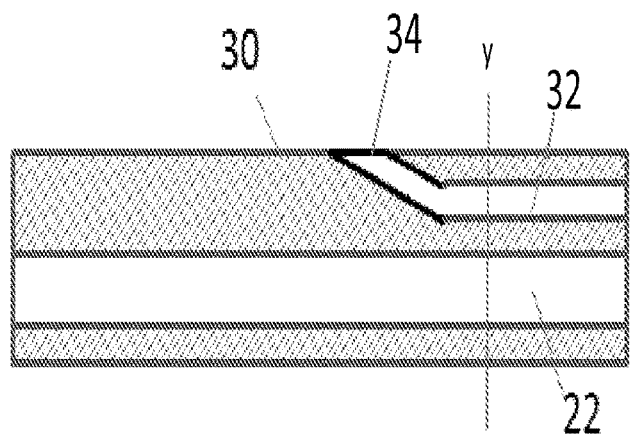
FIG. 3A (Prior Art)
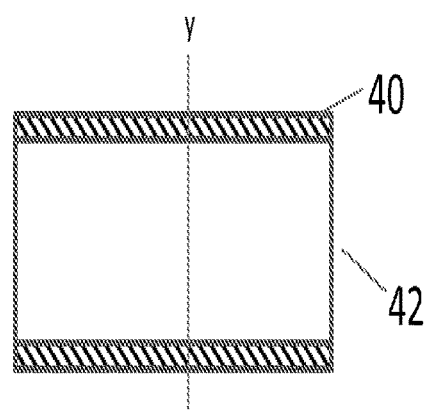
FIG. 3B
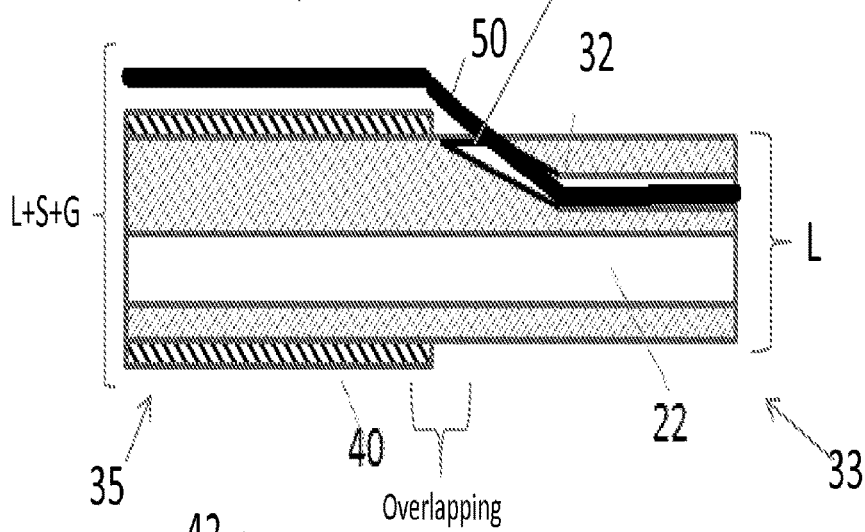
FIG. 3C
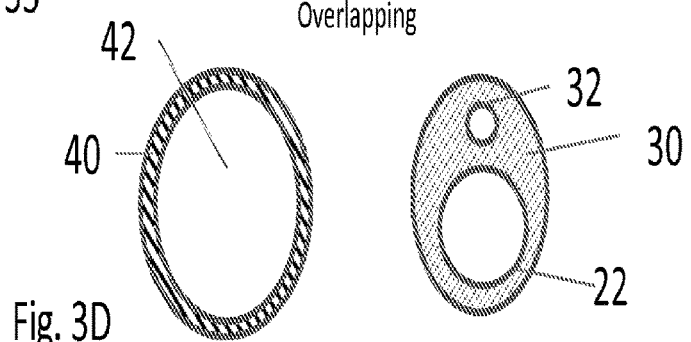
Fig. 3D
FIG. 3E

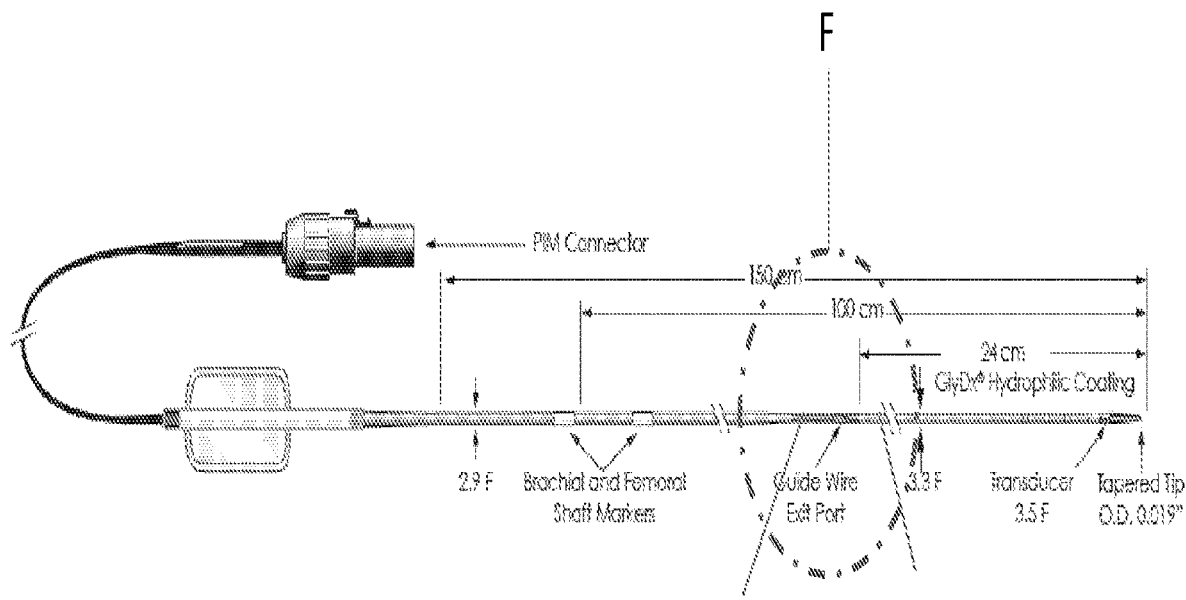

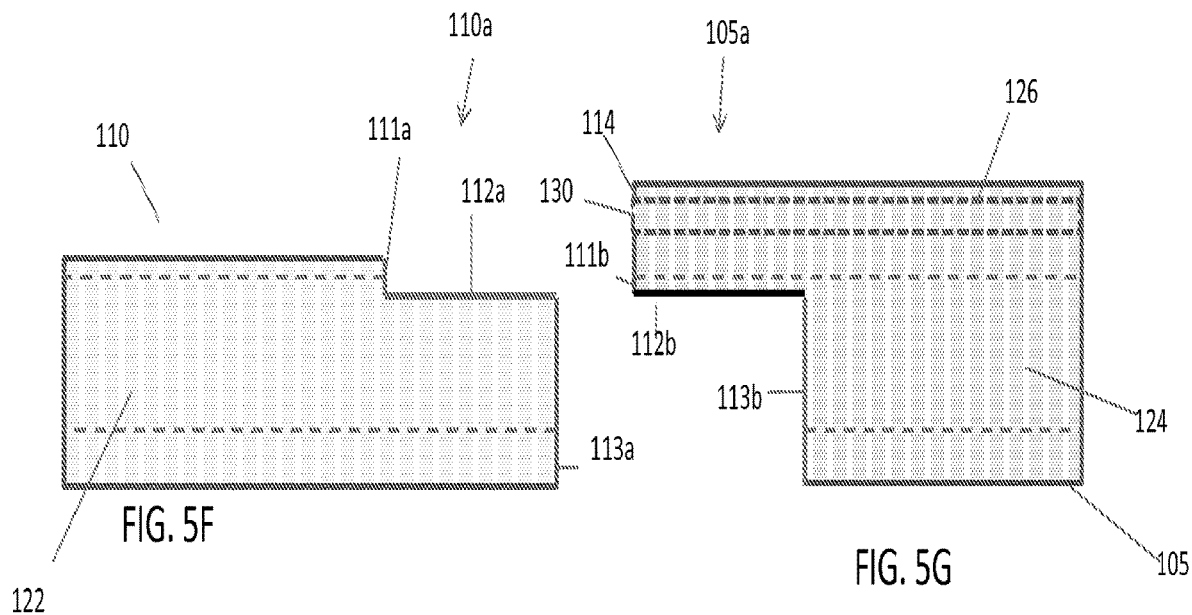
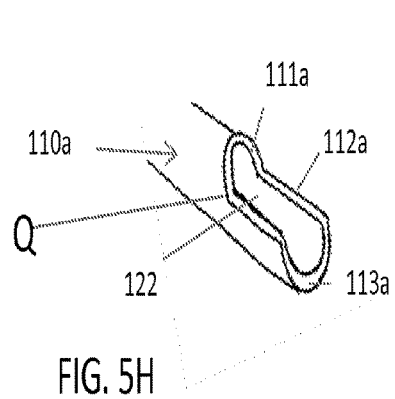
FIG. 5F  FIG. 5G
FIG. 5H  FIG. 5I

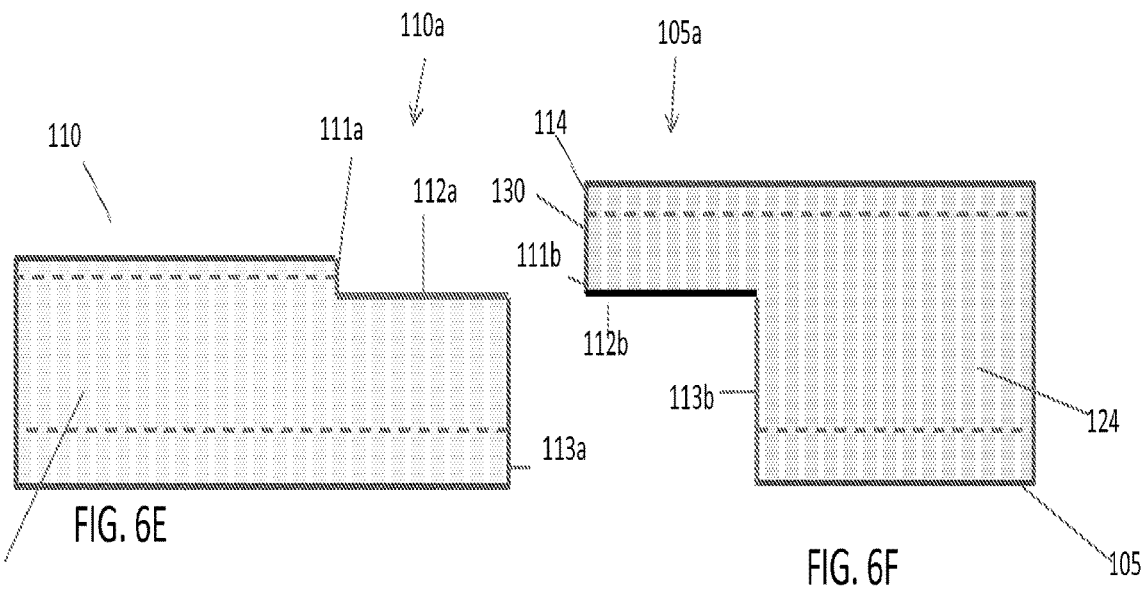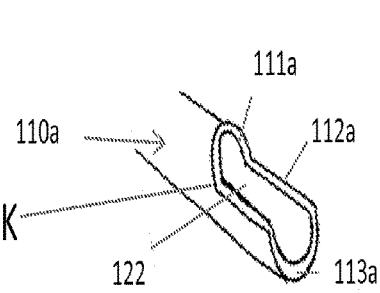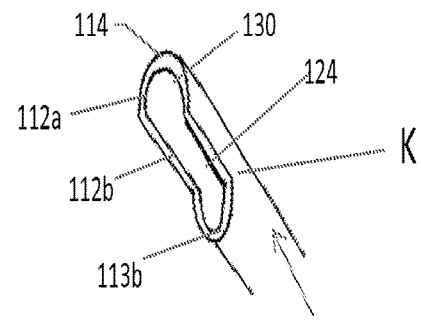
FIG. 6E
FIG. 6F
FIG. 6G
FIG. 6H

SMOOTH TRANSITION CATHETERS

CROSS REFERENCE TO RELATED APPLICATIONS

This application is a continuation of U.S. application Ser. No. 14/108,609, filed Dec. 17, 2013, now issued as U.S. Pat. No. 10,595,820, which claims the benefit of and priority to U.S. Provisional Ser. No. 61/739,855, filed Dec. 20, 2012, each of which is incorporated by reference in its entirety.

TECHNICAL FIELD

The present application generally relates rapid exchange configuration for catheters. The invention provides enhanced designs that improve transitions between components of catheter.

BACKGROUND

Intraluminal devices, such as guidewires and catheters, allow for a variety of disorders of the endovascular to be evaluated and treated without creating an open surgical field. Endovascular procedures typically include passing a guidewire through an access artery (e.g. brachial, femoral, radial) and to a vessel of interest within the vasculature. Once the guidewire is in place, a catheter is guided over the guidewire to perform an intraluminal procedure at the vessel of interest. An intraluminal procedure may require the introduction and exchange of several specialized catheters into the vasculature, which can lead to lengthy procedure times. As a result, changes have been made to the design of the catheters in order to improve their exchangeability and reduce procedure length.

A known catheter design for reducing procedure time is a rapid exchange configuration, which includes a guidewire lumen that only extends through the distal portion of the catheter. Prior to rapid exchange guidewire lumens, catheters often included an over-the-wire lumen that extended the entire length of the catheter device. Due to the long lumen, an over-the-wire catheter requires a guidewire more than twice the length of the catheter. This allows a physician to maintain a grip on the ex vivo portion of the guidewire when exchanging catheters. The long guidewire is cumbersome to handle, causes clutter, and often slows down an already lengthy procedure.

In contrast, a rapid exchange catheter has a guidewire lumen that only extends through the distal portion of the catheter. A typical known rapid exchange configuration includes a substantially L-shaped lumen that begins at a distal tip of the catheter and ends at a guidewire exit port, which is located on a side of the distal portion of the catheter and faces the vessel surface. In this configuration, the guidewire passes through the catheter shaft only for a segment of the length of the shaft, and the catheter can be moved along the guidewire in "monorail" fashion. Because the guidewire lumen is considerably shorter than the overall length of the catheter, a shorter guidewire can be used. For easy handling, the guidewire simply has to be long enough so that the length of the guidewire protruding from the patient is longer than the length of the guidewire lumen of the catheter. This ensures a portion of the guidewire is exposed at all times and may be grasped by the physician.

The current rapid exchange configuration suffers from some drawbacks, however. The rapid exchange design requires a portion of the guidewire to bend within the L-shaped guidewire lumen to exit the guidewire exit port located on the side of the catheter. In addition, the guidewire must bend again once out of the guidewire exit port in order to extend parallel to the proximal portion of the catheter. Because the guidewire exits the side of the catheter and then extends in parallel to the catheter, this configuration increases the vessel diameter requirements (i.e. the vessel must fit the combined diameters of the catheter and the guidewire).

In addition, the various bending of the guidewire may provide push issues or track issues with the catheter as it is being driven over the guidewire. A push issue arises when a proximal portion of a catheter is pushed further into the entry vessel and a distal end does not move the corresponding distance. A track issue arises when the proximal portion is torqued and the distal end does not rotate as expected. Pushing and tracking properly are crucial in negotiating the difficult curves or obstructions in the vasculature.

Thus, there is a need for a rapid exchange catheter with a low profile that reduces guidewire resistance.

SUMMARY

The invention provides catheters having a guidewire exit port that is open in the proximal direction and a substantially straight guidewire lumen. Catheters of the invention allow rapid guidewire exchange and minimal guidewire resistance. Because the guidewire lumen is substantially straight, the guidewire is not required to bend in order to exit the guidewire lumen or bend in order to extend along the proximal portion of the catheter within the vessel. This eliminates guidewire resistance as the catheter is being guided on the guidewire and provides better push and tracking characteristics. In addition, with the rapid exchange configuration of the invention, the exposed guidewire extends parallel to the proximal portion of the catheter without increasing the profile of the combined catheter and guidewire.

According to certain aspects, a catheter with the rapid exchange configuration of the invention includes a proximal portion and a distal portion. The distal portion defines a guidewire lumen, in which a proximal portion of the guidewire lumen is substantially straight. The distal portion also includes a guidewire exit port being open in a proximal direction and leading to the guidewire lumen. The guidewire exit port is configured to receive a guidewire running parallel to the proximal portion. In some embodiments, the distal portion has a cross-section larger than a cross-section of the proximal portion. In this manner, the combined profile of the guidewire and the proximal portion is the same as or smaller than the profile of the distal portion of the catheter. As a result, the portion of the guidewire exiting the distal portion does not increase the vessel diameter requirements.

A catheter with the rapid exchange configuration according to certain embodiments is constructed from a first shaft coupled to a second shaft. The coupled first shaft and second shaft form at least part of the catheter body. The first shaft includes a skived proximal portion and defines a first lumen. The skived proximal portion includes a guidewire exit port being open in the proximal direction. The second shaft includes a skived distal portion and defines a second lumen. The skived distal portion of the second shaft is coupled to the skived proximal portion of the first shaft such that the first lumen and the second lumen form a continuous lumen. In some embodiments, the continuous lumen includes the guidewire lumen, and the guidewire exit port leads to a portion of the continuous lumen. In other embodiments, the first shaft includes a guidewire lumen separate from the continuous lumen, and the guidewire exit port leads to the guidewire lumen.

Concepts of the invention can be applied to any type of catheter. Suitable catheters include, for example, imaging catheters, delivery catheters, and interventional catheters. In particular embodiments, a catheter including concepts of the invention is an imaging catheter. The imaging catheter may include an imaging element positioned on the distal portion of the catheter. The imaging element is a component of an imaging assembly. The imaging assembly can be an ultrasound assembly or an optical coherence tomography assembly.

Other and further aspects and features of the invention will be evident from the following detailed description and accompanying drawings, which are intended to illustrate, not limit, the invention.

BRIEF DESCRIPTION OF DRAWINGS

FIG. 2A depicts the distal end of a proximal portion of a catheter.
FIG. 2B depicts the proximal end of a distal portion of a catheter.
FIG. 2C depicts a proximal portion of FIG. 2A coupled to the distal portion of FIG. 2B via a butt joint.
FIG. 2D depicts a cross-sectional view of the proximal portion of FIG. 2A.
FIG. 2E depicts a cross-sectional view of the distal portion of FIG. 2B.
FIG. 3A depicts a section of a foundation hypotube of a catheter.
FIG. 3B depicts a section of an intermediate hypotube of a catheter.
FIG. 3C depicts the intermediate hypotube of FIG. 3B overlapping the foundation hypotube of FIG. 3A to form the distal and proximal portions of varying flexibility.
FIG. 3D depicts a cross-sectional view of the proximal portion of FIG. 3A.
FIG. 3E depicts a cross-sectional view of the distal portion of FIG. 3B.
FIG. 4 depicts an exemplary phased-array IVUS catheter with the rapid exchange configuration of the invention according to certain embodiments.
FIG. 5F shows the distal end of the proximal portion of a catheter according to certain embodiments of the invention.
FIG. 5G shows the proximal end of the distal portion of a catheter according to certain embodiments of the invention.
FIG. 5H illustrates a skive cut of a proximal portion of the invention according to certain embodiments.

FIG. 5I illustrates a skive cut of a distal portion of the invention according to certain embodiments.
FIG. 6E shows the distal end of the proximal portion of a catheter according to certain embodiments of the invention.
FIG. 6F shows the proximal end of the distal portion of the catheter according to certain embodiments of the invention.
FIG. 6G illustrates a skive cut of a proximal portion according to certain embodiments of the invention.
FIG. 6H illustrates a skive cut of a distal portion according to certain embodiments of the invention.

DETAILED DESCRIPTION

The present invention discloses a rapid exchange configuration for catheters that provides the desired combination of a low profile catheter/guidewire system with minimal to no guidewire resistance. A catheter with the rapid exchange configuration of the invention generally includes a guidewire exit port being open in the proximal direction and leading to a substantially straight guidewire lumen. The proximally facing guidewire exit port and the substantially straight guidewire lumen allow the guidewire to remain straight as it passes through the guidewire lumen. This eliminates the bending of the required by contemporary rapid exchange guidewire lumens. Instead, with the rapid exchange configuration of the invention, the guidewire is able to smoothly transition into and out of the guidewire lumen. The smooth transition of the guidewire reduces guidewire resistance and improves catheter tracking and push capabilities.

As discussed in the Background, current rapid exchange configurations suffer from two major drawbacks. First, the guidewire is required to bend as it extends out of the guidewire exit port and along a proximal portion of the catheter. Second, because the guidewire exit port is located on the side of the catheter, a portion of the guidewire extending out of the guidewire exit port and next to the catheter body increases vessel diameter requirements. For example, the vessel must have a diameter sufficient to support both the full diameter of the catheter and the full diameter of the guidewire running in parallel to catheter. In order to better understand aspects and benefits of the current invention, a brief discussion of prior art rapid exchange catheters and the various mechanical elements thereof, in general, is provided below.

Figure 1:
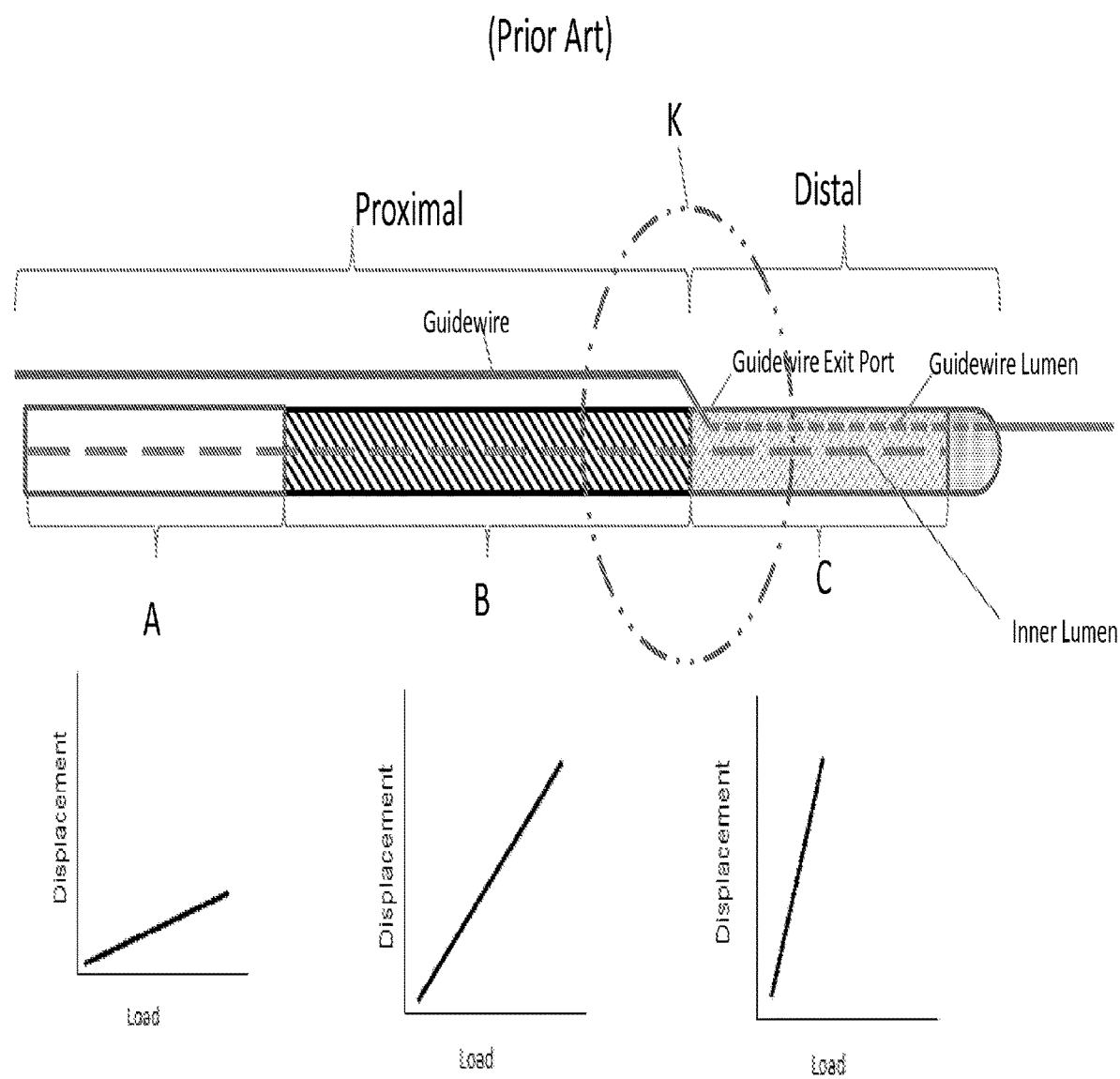
FIG. 1 depicts a prior art catheter.

FIG. 1 depicts a prior art catheter. As shown in FIG. 1, the catheter includes a proximal portion and a distal portion. The catheter is shown with a guidewire disposed therein. The catheter rides along the guidewire extending through the distal portion. A portion of the guidewire exits through a guidewire exit port and extends along the proximal portion of the catheter.

A common problem of prior art catheters is their rapid exchange configuration, which is highlighted in the area enclosed by circle K of FIG. 1. The rapid exchange configuration includes the shape of the rapid exchange guidewire lumen and the location of the guidewire exit port. Because the guidewire exit port is located on a side of the catheter body, the guidewire lumen requires a bend to direct the guidewire from the distal tip to the guidewire exit port. The bend ultimate causes a guidewire extending through the lumen to bend. In addition, the location of the guidewire exit port requires the guidewire to bend again upon exiting the guidewire exit port so that the guidewire extends parallel and alongside catheter body. FIG. 2C highlights the contemporary guidewire lumen and guidewire exit port. The distal portion 15 includes guidewire lumen 6. The guidewire lumen 6 includes bend 17 and leads to guidewire exit port 2 located on the side of the distal portion 15. The guidewire 50 extending through the lumen 6 and out of the guidewire exit port 2 must bend twice 21 and 23 in order to run alongside the proximal portion 13. This bending of the guidewire can cause resistance against the catheter as it is pushed distally along or rotated with respect to the guidewire, which may result in push and tracking issues.

Most catheters include at least one inner lumen, in which one or more functional elements are housed or driven there through. For example, imaging catheters often utilize the inner lumen to house transmission lines that connect an imaging element located on the distal end of the catheter to an imaging instrument connected to a proximal end of the catheter. Delivery catheters, on the other hand, often use the inner lumen to contain an implant deployment mechanism. For example, a push rod can be driven through the inner lumen to distally deploy an implant out of a distal end of the catheter and into a vessel. Aspiration catheters utilize the inner lumen as an aspiration channel, through which debris and blood clots can be removed from the vessel.

The proximal portion and the distal portion of most catheters act to create a catheter body of variable stiffness and flexibility. The distal portion is typically quite flexible. The proximal portion, as shown in FIG. 1, may include a stiff section A and an intermediate section B, which has flexibility somewhere between the stiff portion and a flexible distal portion. Alternatively, the proximal portion may be a hypotube of uniform flexibility. The stiffness/flexibility is shown graphically next to each section as correlation between load and lateral displacement. The stiff portion A includes a small correlation between load and lateral displacement. In other words, when a transverse force is exerted on the proximal end, the proximal end only flexes a small amount. In contrast, the distal end is quite flexible and experiences a large amount of lateral displacement with a relatively small amount of applied load.

In order to create the catheter body of varying stiffness and flexibility, the catheter is generally formed from a combination of components fused together or overlapping. That, the stiff portion, intermediate section, and the distal portion are often separate individual tubes or parts that are fused together or overlapped to form the elongate catheter body with desired mechanical properties. For example, the stiff portion of many catheters includes a stiff hollow tube (hypotube) that is only slightly flexible and has excellent compressional strength, allowing a physician to deliver force laterally along the catheter. Hypotubes may be constructed from standard metals, such as stainless steel, or from memory metals, such as nitinol, an alloy of nickel and titanium. Hypotubes may also be constructed from polymers such as the polymer sold under the trademark PEBAX®, nylon, HDPE, and the polymer sold under the trademark PEEK. The intermediate sections are often also hypotubes and are constructed from polymers with moderate stiffness, such as polyamides, to provide transitional flexibility between the proximal and distal ends. The distal end of the intraluminal device is typically constructed from a flexible polymer hypotube with good kink resistance, such as a fluoropolymer.

A common design consideration for joining portions of a catheter includes aligning lumens of the individual sections. For example, in order to create a continuous inner lumen extending the entire length of the catheter, the lumens of the individual sections must be aligned. Another design consideration is the tensile strength of catheter at the joint between two different portions. A catheter design having insufficient tensile strength can result in catheter failure. For example, when catheter is under tension while being proximally retracted from within the patient's body lumen, a catheter body having insufficient tensile strength may partially or completely tear at the joint between two portions. This can result in the potentially lethal dislocation of the catheter distal portion.

Another design consideration for joining the distal and proximal portions of the catheter includes the rapid exchange profile of the catheter. The rapid exchange profile is the combined profile of both the guidewire and catheter having a rapid exchange configuration. One must consider the catheter diameter and the diameter of the guidewire when determining whether the system can enter a vessel of interest. Vessels of interest are often inherently small and can have further reduced diameters due to the build up of atheroma material such as plaque. As such, it is desirable to have a small rapid exchange profile, so that the catheter can access more vessels. The type of transition can affect the overall rapid exchange profile of the catheter.

The following describes common ways for transitioning between the distal and proximal portions of varying flexibility, which is also the portion of the catheter enclosed by the circled K of FIG. 1. The resulting rapid exchange profile is also discussed.

One known way to transition between the distal and proximal portions of a catheter is to form a butt joint. A butt joint is formed by abutting the flat ends of the distal and proximal portions squarely together. Generally, an intermediate hypotube of the proximal portion is coupled directly coupled to a flexible hypotube of the distal portion and then fused together to form a continuous elongate catheter body. FIGS. 2A-2E depict formation of a butt joint between a flexible distal portion and a stiffer proximal portion of a catheter. FIG. 2A shows the distal end 10 of a proximal portion 13 with an inner lumen 4. FIG. 2D shows a cross-sectional view of the proximal portion 13 at the y-axis of FIG. 2A. FIG. 2B shows a proximal end 20 of the distal portion 15 with an inner lumen 8 and a guidewire lumen 6. FIG. 2E shows a cross-sectional view of the distal portion 15 at the y-axis of FIG. 2B. The guidewire lumen 6 includes a bend 17 that leads to a guidewire exit port 2 on a side of the distal portion 20. To form the butt joint, a distal surface 10*a* of the proximal portion 13 is placed flush against a proximal surface 20*a* of the distal portion 15, as shown in FIG. 2C. The inner lumen 4 of the proximal portion 13 is matched up against the inner lumen 8 of the proximal portion 10. Once properly abutted, the proximal portion 13 is fused to the distal portion 15 using known catheter fusing techniques.

FIG. 2C also shows the rapid exchange profile of the catheter with the butt joint configuration. As shown, a portion of the guidewire 50 is extending through the guidewire lumen 6. Another portion of the guidewire 50 exits through the guidewire exit port 2 and is extending parallel to the proximal portion 13. Because the guidewire 50 exits the side of the distal portion, the rapid exchange profile includes the diameter of both the guidewire and the catheter. That is, the rapid exchange profile includes the diameter (L) of the catheter plus the diameter (G) of the guidewire (L+G).

A problem associated with the butt joint design is that the butt joint has a low tensile strength, and therefore poses a risk of joint failure and dislocation of the distal portion. An alternative design for transitioning between the distal and proximal portions that provides variable flexibility and a high tensile strength is an overlapping design. The overlapping design includes overlapping hypotubes or applying coating layers to create the flexible distal portion and the stiffer proximal portion. For example, a flexible hypotube extending the fully length of the catheter is provided as a foundation. To create an intermediate proximal section (Section B in FIG. 1), a polymer coating or hypotube is placed over a portion of the flexible hypotube leaving only the distal portion exposed. This creates the flexible distal portion and an intermediate proximal portion. To create the stiff proximal section (Section A in FIG. 1), an additional polymer coating or hypotube is placed over the proximal end of the proximal portion leaving the intermediate proximal section B exposed.

FIGS. 3A-3E depict formation of an overlapping transition between a flexible distal portion and a stiffer proximal portion of a catheter. FIG. 3A shows a foundation hypotube 30. Although not shown, the foundation hypotube 30 extends the entire length of the catheter body. The foundation hypotube 30 includes an inner lumen 22 and a guidewire lumen 32. FIG. 3E shows a cross-sectional view of the foundation hypotube 30 at the y-axis of FIG. 3A. FIG. 3B shows an intermediate hypotube 40. The intermediate hypotube 40 can be used to create the intermediate section B of the proximal portion (See FIG. 1). The intermediate hypotube 40 includes a center lumen 42. FIG. 3D shows a cross-sectional view of the intermediate hypotube 40. To form the catheter with varying flexibility, the foundation hypotube 30 is disposed within the center lumen 42 of the intermediate hypotube 40, leaving the distal portion of the foundation hypotube 30 exposed, as shown in FIG. 3C. The foundation hypotube 30 and the intermediate hypotube 40 can be fused together with heat or by adhesive. The exposed foundation hypotube 30 forms flexible distal portion 33 and the overlapping hypotubes 30 and 40 form the intermediate proximal portion 35. Instead of the using an intermediate hypotube 40, the intermediate proximal portion 35 can be formed by applying a polymer coating to the foundation tube 30, leaving the distal portion exposed.

FIG. 3C also shows the rapid exchange profile of the catheter with the overlapping configuration. Like the butt-joint design, the catheter guidewire 50 exits the side of the distal portion and extends along the length of the proximal portion of the catheter. However, the overlapping catheter body has a larger diameter as compared to the butt-joint configuration because the profile of the proximal portion includes the diameter (L) of the foundation catheter body plus the thickness (S) of the intermediate hypotube. Thus, the overall rapid exchange profile includes the diameter (L) of the foundation hypotube 30, the thickness (S) of the intermediate hypotube 40, and the diameter (G) of the guidewire 50.

While the overlapping design provides a catheter having variable flexibility with high tensile strength, the overlapping configuration undesirably increases the rapid exchange profile. Because of the increased rapid exchange profile, the overlapping design limits the accessibility of the catheter within the vasculature.

Catheters of the invention overcome the shortcomings of the prior art by providing a substantially straight guidewire lumen and a proximally facing guidewire exit port. In addition, some embodiments of the present invention include a smaller rapid exchange profile than possible with the prior art catheters. Furthermore, certain embodiments achieve the smaller rapid exchange profile while also maintaining the high tensile strength between a flexible distal portion and a stiffer proximal portion.

The concepts of the invention may be applied to any intraluminal catheter, which may include intravascular catheters and urological catheters. In certain embodiments, the concepts of the invention are applied to rapid exchange catheters, which have guidewire lumens only extending in the distal portion. A catheter of the invention may be an imaging catheter, a delivery catheter, or an interventional catheter. Delivery catheters typically deliver a medical device (e.g. stent, filter, or plug) into the body. Interventional catheters are often used to morcellate or ablate diseased tissue. Catheter bodies intended for intravascular introduction, will typically have a length in the range from 50 cm to 200 cm and an outer diameter in the range from 1 French to 12 French (0.33 mm: 1 French), usually from 3 French to 9 French. In the case of coronary catheters, the length is typically in the range from 125 cm to 200 cm, the diameter is preferably below 8 French, more preferably below 7 French, and most preferably in the range from 2 French to 7 French. A distal portion of a catheter may range from 5 cm to 25 cm and a proximal portion may range from 50 to about 200 cm. Intermediate sections of the proximal portion may range from 25-125 cm.

In some embodiments, the catheter will be an imaging or sensing catheter. Imaging catheters allow a physician to acquire images of tissues from within a lumen, e.g., a blood vessel. Often it is instructive to image a tissue prior to treatment, e.g., with angioplasty or drugs. The image may be obtained with acoustic waves, i.e., ultrasound, or the image may be obtained with light. Thus, the invention includes intravascular ultrasound (IVUS), optical coherence tomography (OCT), and intravascular magnetic resonance imaging (IVMRI), in addition to other intravascular imaging techniques. Systems for IVUS are discussed in U.S. Pat. No. 5,771,895; U.S. Pub. 2009/0284332; U.S. Pub. 2009/0195514 A1; U.S. Pub. 2007/0232933; and U.S. Pub. 2005/0249391, the contents of each of which are hereby incorporated by reference in their entirety. The imaging catheters may use any configuration, such as phased array, forward-looking, rotational pullback, etc. Sensing catheters, such as flow (Doppler), pressure, temperature, or blood oxygenation-sensing catheters will also benefit from variable stiffness midsections.

An exemplary phased-array IVUS catheter with the improved rapid exchange configuration of the invention is illustrated in FIG. 4. The area enclosed by circle F highlights the transition between the distal portion and proximal portion and a rapid exchange configuration of the invention. Various embodiments of the transition between the distal portion and the proximal portion and embodiments of the rapid exchange configuration of the invention are described hereinafter.

Figure 5A:
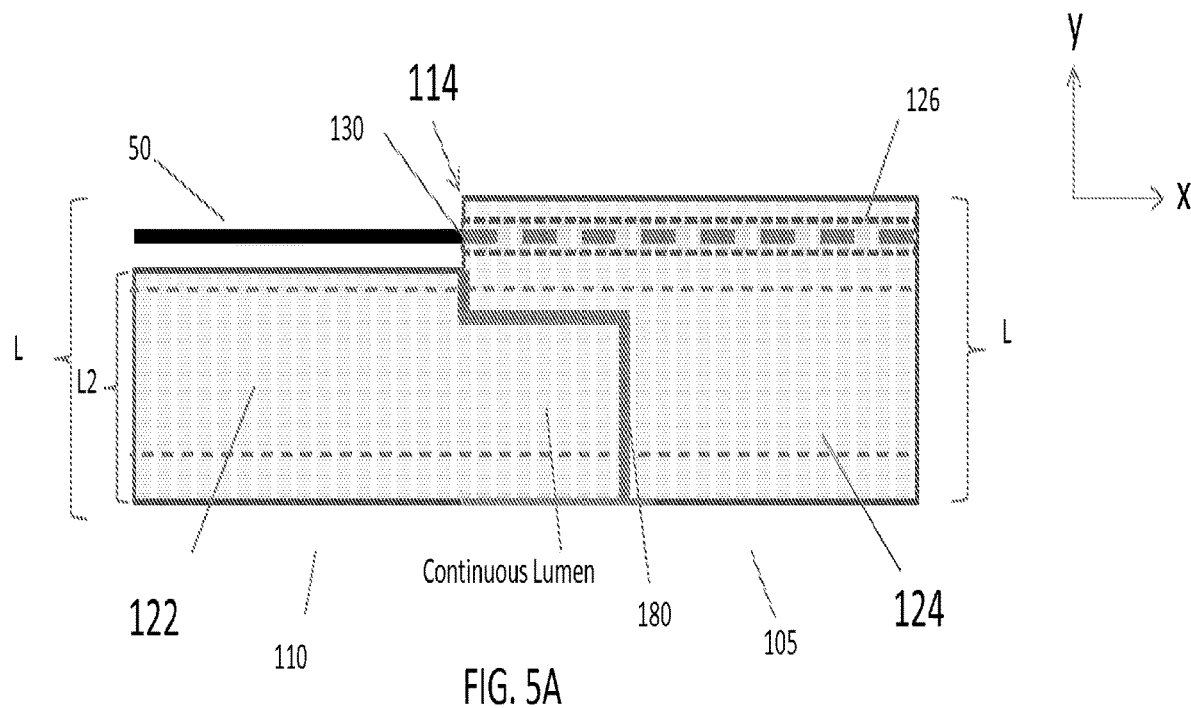
FIG. 5A shows the transition between a distal portion and a proximal portion of a catheter having the rapid exchange configuration of the invention according to certain embodiments.

FIG. 5A shows the transition between a distal portion 105 and a proximal portion 110 of a catheter having the rapid exchange configuration according to one embodiment. The distal portion 105 and the proximal portion 110 can be formed from one continuous shaft or two shafts coupled (e.g. fused) together at a joint. As shown, the distal portion 105 and the proximal portion 110 are two separate shafts coupled together to form the catheter body. Preferably, the distal portion 105 is a flexible hypotube fabricated from a flexible polymer (as discussed previously), and the proximal portion 110 is a hypotube of moderate stiffness (such as the previously discussed hypotubes for the intermediate section B).

As discussed, certain aspects of the invention involve forming a joint between a shaft of the distal portion 105 and a shaft of the proximal portion 110 to create the rapid exchange configuration shown in FIG. 5A. FIG. 5F shows a distal end 110*a* of the shaft of the proximal portion 110 according to certain embodiments. The proximal portion 110 defines an inner lumen 122 and includes a distal end 110*a*. FIG. 5G shows a proximal end 105*a* of the shaft of the distal portion 105 according to certain embodiments. The distal portion 105 defines an inner lumen 124 and a guidewire lumen 126. To form the catheter body, the distal end 110*a* of the proximal portion 110 is coupled to the proximal end 105*a* of the distal portion 105. Preferably, the distal portion 105 and the proximal portion 110 are joined so that the inner lumen 124 of the distal portion 105 and the inner lumen 122 of the proximal portion 110 align to form the continuous lumen shown in FIG. 5A.

Figure 5B:
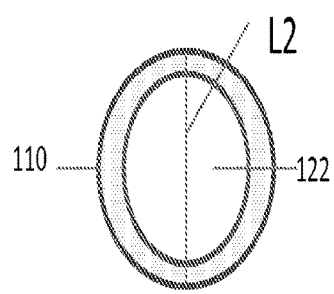
FIG. 5B illustrates a cross-sectional view of the proximal portion shown in FIG. 5A.
Figure 5C:
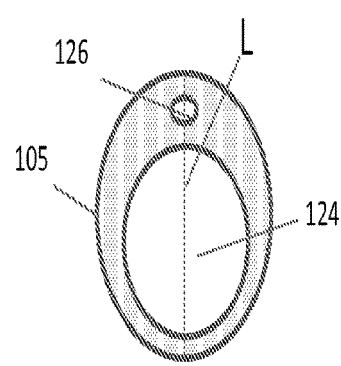
FIG. 5C illustrates a cross-sectional view of the distal portion shown in FIG. 5A.
Figure 5D:
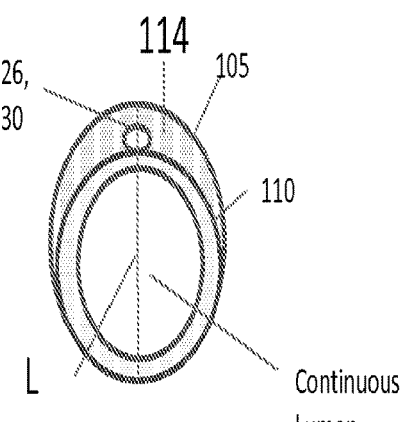
FIG. 5D illustrates a distal-facing view of the proximal portion extending proximally from the distal portion as shown in FIG. 5A.

A diameter L2 of the proximal portion 110 is smaller than the diameter L of the distal portion 105. This orientation allows a section of the distal portion 105 to extend vertically (in the y-direction) beyond the proximal portion 110 as joined to the distal portion 105. The extended section of the distal portion 105 forms the proximal face 114 of the distal portion 105. FIG. 5B illustrates a cross sectional view of the proximal portion 110 as shown in 5A. FIG. 5C illustrates a cross sectional view of the distal portion 105 as shown in FIG. 5A. FIG. 5D illustrates a distal-facing view of the proximal portion 110 extending proximally from the distal portion 105 as shown in 5A. As shown in FIG. 5D, the cross-section of the proximal portion 110 completely aligns with a section of the distal portion 105. In this manner, the maximum diameter of the combined proximal and distal portions is the diameter L of the distal portion 105.

Figure 5E:
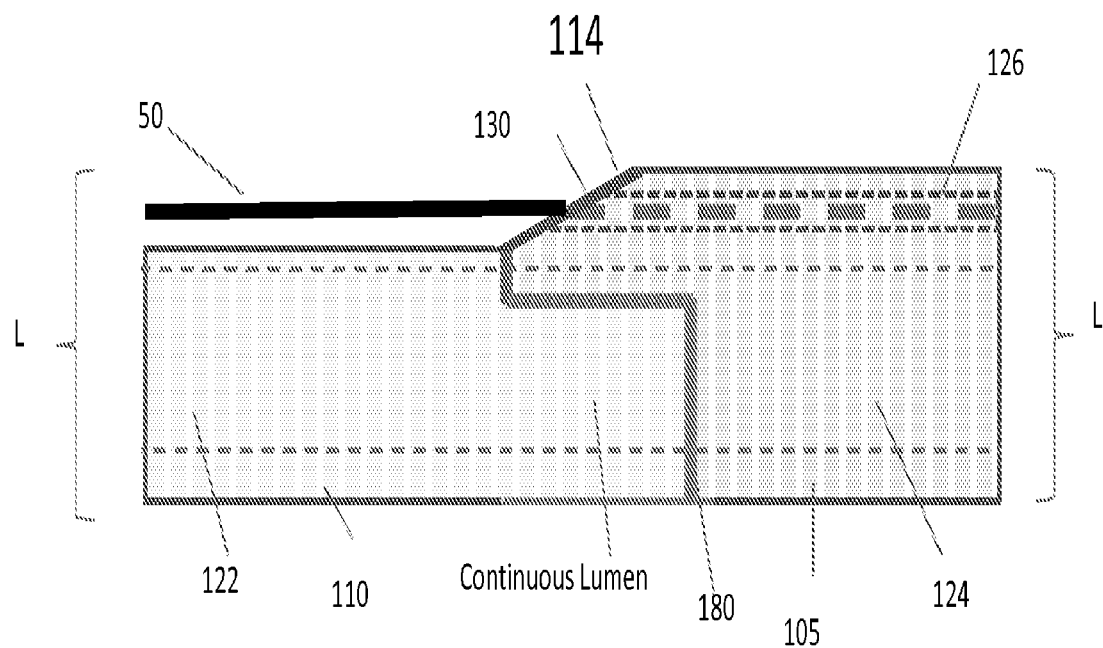
FIG. 5E shows an alternative embodiment of the transition between the distal portion and proximal portion of the catheter shown in FIG. 5A.

As discussed, the section of the distal portion 105 extending vertically above the proximal portion 110 (i.e. the section of the distal portion 105 that is not directly aligned with and facing the proximal portion 110) forms the proximal face 114 of the distal portion 105. The proximal face 114 defines a guidewire exit port 130, which leads to guidewire lumen 126. FIG. 5E depicts another embodiment of the proximal face 114 that has been angled to provide a smoother device profile.

As shown in FIG. 5A, the guidewire exit port 130 is open in the proximal direction and leads to a guidewire lumen 126. In certain embodiments, at least the proximal portion of the guidewire lumen 126 is substantially straight. In certain embodiments, the entire length of the guidewire lumen is substantially straight 126. Alternatively, a distal portion of the guidewire lumen may slight curve to, for example, combine the guidewire lumen 126 with the continuous lumen or provide a guidewire entry port at the center of a distal tip of the device.

A benefit of the proximally facing guidewire exit port 130 leading to a substantially straight guidewire lumen 126, as shown in FIGS. 5A and 5E, is that the guidewire 50 does not have to bend to exit the guidewire lumen 126. In addition, the guidewire 50 does not have to bend after exiting the guidewire exit port to extend alongside the proximal portion 110. Rather, the guidewire 50 maintains a substantially straight shape as it extends through the guidewire lumen 126 and out of the guidewire exit port 130. This configuration reduces resistance of the guidewire 50 as the catheter is driven over the guidewire 50 in the distal or proximal directions.

Another benefit of the catheter design shown in FIGS. 5A and 5E is the rapid exchange profile (i.e. the combined profile of the catheter and guidewire). Because the rapid exchange configuration does not require the guidewire 50 to exit through a guidewire exit port located on the side of the distal portion 105, the guidewire 50 does not increase the rapid exchange profile of the device. Rather, the guidewire 50 exits proximally from the guidewire exit port 130 in a linear fashion and runs parallel and along the proximal portion 110. Thus, the rapid exchange profile of the device equals the diameter L of the distal portion 110. As a result, devices having this rapid exchange configuration of the invention have an overall lower profile than the prior art rapid exchange catheters shown in FIGS. 1, 2C and 3C. The lower profile allows a physician to access the smaller vessels of the vasculature with ease.

In addition, the distal portion 105 and the proximal portion 110 of the embodiment shown in FIGS. 5A and 5B, define at least one inner lumen that extends continuously between the distal portion and the proximal portion 110. The inner continuous lumen may extend the entire length of the catheter. The continuous lumen may provide any function, such as housing the transmission lines to provide energy to an imaging element, sensor, or ablation element located at the distal end of the device and to return signals from any of those elements. As another example, the continuous lumen can be used to house a morcellating tool that can be extended out of the distal end of the catheter to morcellate diseased tissue.

Figure 6A:
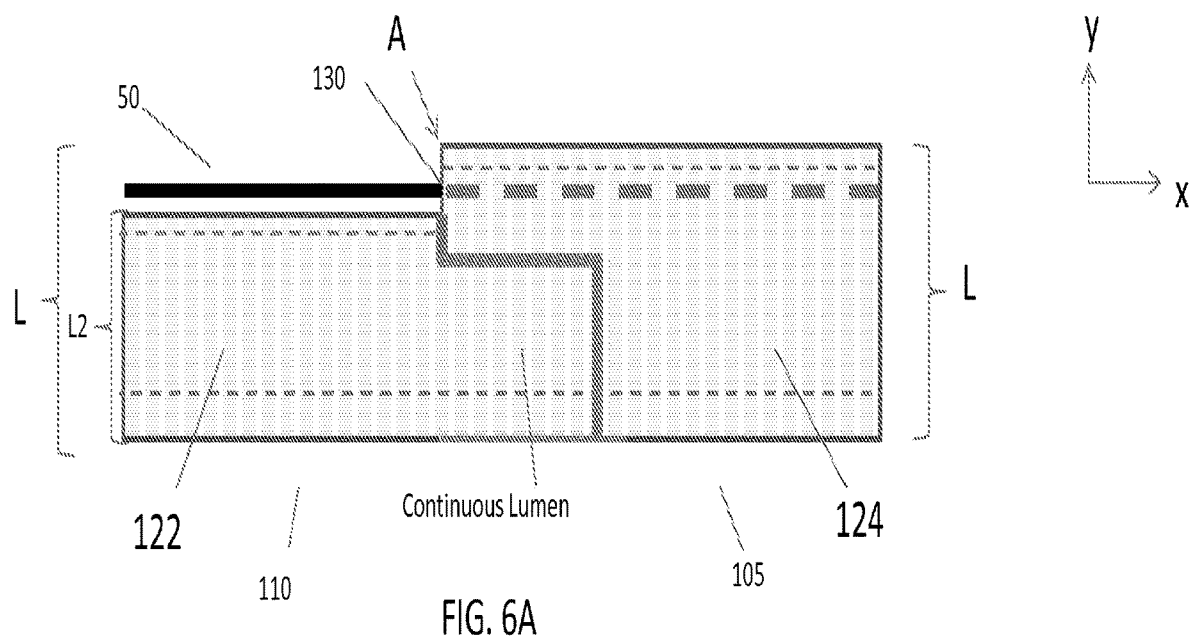
FIG. 6A shows the transition between a distal portion and a proximal portion of a catheter having the rapid exchange configuration of the invention according to other embodiments.

FIG. 6A shows the transition between a distal portion 105 and a proximal portion 110 of a catheter having the rapid exchange configuration according to another embodiment. The distal portion 105 and the proximal portion 110 can be formed from one continuous shaft or two shafts coupled (e.g. fused) together at a joint. As shown, the distal portion 105 and the proximal portion 110 are two separate shafts coupled together to form the catheter body. Preferably, the distal portion 105 is a flexible hypotube fabricated from a flexible polymer (as discussed previously), and the proximal portion 110 is a hypotube of moderate stiffness (such as the previously discussed hypotubes for the intermediate section).

As discussed, certain aspects of the invention involve forming a joint between a shaft of the distal portion 105 and a shaft of the proximal portion 110 to create the rapid exchange configuration shown in FIG. 6A. FIG. 6E shows the shaft of the proximal portion 110 according to certain embodiments. The proximal portion 110 defines an inner lumen 122 and includes a distal end 110*a*. FIG. 6F shows the shaft of the distal portion 110 according to certain embodiments. The distal portion 105 defines an inner lumen 124. In this aspect, the inner lumen 124 is the guidewire lumen and forms the continuous lumen between the distal portion 105 and proximal portion 120. In addition, the distal portion 105 includes a proximal end 105*a*. To form the catheter body, the distal end 110*a* of the proximal portion 110 is coupled to the proximal end 105*a* of the distal portion 105.

A diameter L2 of the proximal portion 110 is smaller than the diameter L of the distal portion 105. In addition, the inner lumen 124 of the distal portion 105 is larger than the inner lumen 122 of the proximal portion 105. Also, the distal portion 105 and the proximal portion 110 are joined so that the inner lumen 124 of the distal portion 105 at least partially aligns with the inner lumen 122 of the proximal portion 110 to form the continuous lumen shown in FIG. 6A. This orientation allows a section of the distal portion 105, which includes a section of the inner lumen 124, to extend vertically (in the y-direction) beyond the proximal portion 110 as joined to the distal portion 105. The extended section of the distal portion 105 forms the proximal face 114 of the distal portion 105. An extended section of the inner lumen 124 forms a guidewire opening 130 on the proximal face 114.

The guidewire opening 130 leads to the inner lumen 124 of the distal portion 124, which is a part of the continuous lumen. Thus, in this embodiment, the inner lumen 124 of the continuous lumen is also the guidewire lumen. Merging the guidewire lumen with the inner lumen reduces the complexity of the shaft of the distal portion 105. Instead of a shaft with a separate guidewire lumen and a separate inner lumen, a common hypotube with a single lumen can be used. In other words, the design shown in FIG. 6A does not require that the distal portion 105 include a guidewire lumen separate from the inner lumen 124, and the design can be made with standard commercially available hypotubes.

Figure 6B:
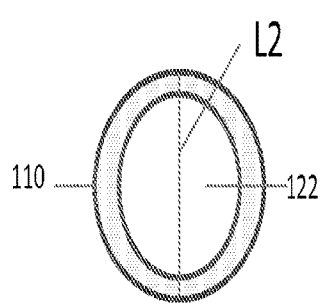
FIG. 6B illustrates a cross-sectional view of the proximal portion shown in FIG. 6A.
Figure 6C:
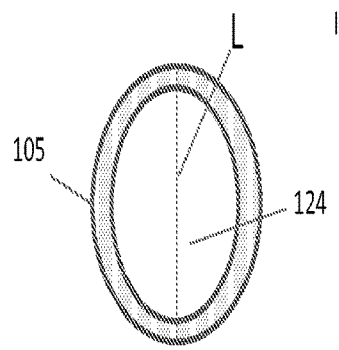
FIG. 6C illustrates a cross-sectional view of the distal portion shown in FIG. 6A.
Figure 6D:
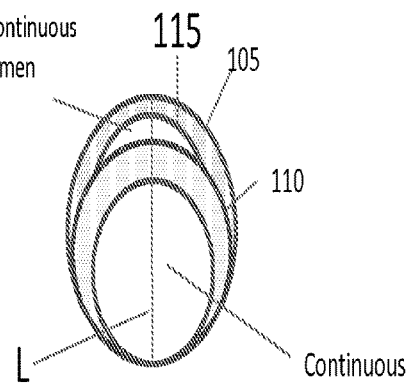
FIG. 6D illustrates a distal-facing view of the proximal portion extending proximally from the distal portion as shown in FIG. 6A.

FIG. 6B illustrates a cross sectional view of the proximal portion 110 shown in FIG. 6A. FIG. 6C illustrate a cross sectional view of the distal portion 105 shown in FIG. 6A. FIG. 6E shows a distal-facing view of the proximal portion 110 extending proximally from the distal portion 105 shown in FIG. 6A. As shown in FIG. 6D, the cross-sectional view of the proximal portion 110 completely aligns with a section the distal portion 105. In this manner, the maximum diameter of the device is the diameter L of the distal portion 105. As discussed, the section of the distal portion 105 extending vertically above the proximal portion 110 (i.e. the portion is not directly aligned with and facing the proximal portion 110) forms the proximal face 114 of the distal portion 105. The proximal face 114 defines a guidewire exit port 130, which leads to inner lumen 124 of the continuous lumen. The proximal face 114 as shown in FIG. 6A may be angled like the proximal face as shown in FIG. 5E to provide a smoother device profile.

As shown in FIG. 6A, the guidewire exit port 130 is open in the proximal direction and leads to inner lumen 124 of the continuous lumen. In certain embodiments, at least the proximal portion of the inner lumen 124 is substantially straight. In certain embodiments, the entire length of the inner lumen 124 is substantially straight. Alternatively, a distal portion of the inner lumen 124 may slight curve to provide a guidewire entry port at the center of a distal tip of the device.

A benefit of the proximally facing guidewire exit port 130 leading to the substantially straight inner lumen 124 of the continuous lumen, as shown in FIG. 6A, is that the guidewire 50 does not have to bend to exit the inner lumen 124. In addition, the guidewire 50 does not have to bend after exiting the guidewire exit port to extend alongside the proximal portion 110. Rather, the guidewire 50 maintains a substantially straight shape as it extends through the inner lumen 124 and out of the guidewire exit port 130. This configuration reduces resistance of the guidewire 50 as the catheter is driven over the guidewire 50 in the distal or proximal directions.

Another benefit of the catheter design shown in FIG. 6A is the rapid exchange profile (i.e. the combined profile of the catheter and guidewire). Because the rapid exchange configuration does not require the guidewire 50 to exit through a guidewire exit port located on the side of the distal portion 105, the guidewire 50 does not increase the rapid exchange profile of the device. Rather, the guidewire 50 exits proximally from the guidewire exit port 130 in a linear fashion and runs parallel and along the proximal portion 110. Thus, the rapid exchange profile of the device equals the diameter L of the distal portion 110. As a result, devices having this rapid exchange configuration of the invention have an overall lower profile than the prior art rapid exchange catheters shown in FIGS. 1, 2C and 3C. The lower profile allows a physician to access the smaller vessels of the vasculature with ease.

In certain embodiments, the invention provides for joining the distal portion 105 and the proximal portion 110 in a segmented fashion. For example, the distal portion 105 and the proximal portion 110 are shown joined in a segmented fashion in FIGS. 5A, 5E, and 6A. In order to produce a segmented joint of the invention, the distal portion 105 and the proximal portion 110 are skived in a complementary orientation that allows the proximal end 105a of the distal portion 105 to overlap with the distal end 110a of the proximal portion 110. Skiving means cutting out a notch across the hypotube, and is best exemplified in FIGS. 5H, 5I, 6G, and 6H. Preferably and as shown, the notch is sliced off distal portion 105 and the proximal portion 105 at a 90.degree. angle (shown as Q). However, other angles can be used, including 91.degree.-135.degree. angles.

Due to the skiving of the distal portion 105 and the proximal portion 110, a plurality of complementary binding surfaces are formed that act to strengthen the joint between the distal portion 105 and proximal portion 110. For example, skived distal end 110a of the proximal portion 110 includes binding surfaces 111a, 112a, and 113a that are complementary to the binding surfaces 111b, 112b, and 113b of the skived proximal end 105a of the distal portion 105, respectively (See FIGS. 5H, 5I, 6G, and 6H). To form the segmented joint, the binding surfaces of the proximal portion 110 are coupled to their complementary binding surfaces of the distal portion 105. The more complementary binding surfaces, the greater the tensile strength of the joint between the distal portion 105 and proximal portion 110. The resulting joint of the distal portion 105 and the proximal portion 110 is shown as bolded line 180 in FIGS. 5A, 5E, and 6A.

Any technique known in the art can be utilized to couple the proximal portion to the distal portion of the catheter. Typically, the various shafts of a catheter are coupled via heat fusing. An exemplary technique for fusing includes holding the shafts of the distal portion and the proximal portion together and placing one or more mandrels within the inner lumen and/or guidewire lumen. The mandrels are preferably the shape and size of the lumens and are coated with a non-stick coating. The non-stick coating can be a polytetrafluoroethylene (PTFE) or a paralene coating. With the distal and proximal portions held together along with the mandrels disposed therein, heat is applied to the joint of the distal and proximal portions, thereby fusing the shafts together. Once the shafts are fused together, the mandrels are removed, and the outer portion of the joint can be shaped as desired to form a smooth, consistent joint. One example of shaping includes angling the proximal end face of the distal portion as shown in FIG. 5C.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. An intraluminal catheter, comprising:
a catheter body configured to be positioned within a body lumen of a patient,
wherein the catheter body comprises a proximal portion coupled to a distal portion, a first side, and an opposite second side,
wherein the proximal portion comprises a first material, a first diameter, a first outer surface,
wherein the distal portion comprises a different second material, a second diameter, a second outer surface,
wherein the first diameter is smaller than the second diameter,
wherein the first outer surface of the proximal portion and the second outer surface of the distal portion are aligned on the first side of the catheter body,
wherein the first outer surface of the proximal portion and the second outer surface of the distal portion are unaligned on the second side of the catheter body by the first diameter of the proximal portion and the second diameter of the distal portion,
wherein the first diameter of the proximal portion defines a space for a guidewire to extend alongside the first material of the proximal portion and outside of the catheter body on the second side of the catheter body,
wherein the second diameter of the distal portion defines a guidewire lumen for the guidewire to extend alongside the second material of the distal portion and inside of the catheter body on the second side of the catheter body,
wherein the guidewire lumen defined by the second diameter is aligned with the space for the guidewire defined by the first diameter,
wherein the second material defines the second outer surface of the distal portion, the guidewire lumen, and an inner lumen distinct from the guidewire lumen,
wherein a portion of the second material is disposed between the guidewire lumen and the inner lumen along an entire length of the guidewire lumen,
wherein an opening of the guidewire lumen is longitudinally co-located with a transition between the first material of the proximal portion and the second material of the distal portion.

2. The intraluminal catheter of claim 1, wherein the first material of the proximal portion defines an additional inner lumen continuous with the inner lumen.

3. The intraluminal catheter of claim 1, wherein a distal end of the proximal portion and a proximal end of the distal portion are skived, and wherein the skived ends are coupled.

4. The intraluminal catheter of claim 3, wherein the coupling comprises a heat fusion joint.

5. The intraluminal catheter of claim 1, wherein the guidewire lumen is arranged such that the guidewire can enter, extend through, and exit the guidewire lumen without bending.

6. The intraluminal catheter of claim 1, wherein the proximal portion is arranged such that a combined diameter of the guidewire and the proximal portion is the same as or smaller than the second diameter of the distal portion.

7. The intraluminal catheter of claim 1, wherein the catheter comprises an imaging catheter, a delivery catheter, or an interventional catheter.

8. The intraluminal catheter of claim 1, wherein the first material comprises a first polymer and the second material comprises a second polymer different from the first polymer.

9. The intraluminal catheter of claim 8, wherein the distal portion is more flexible than the proximal portion.

10. The intraluminal catheter of claim 8, wherein the second material comprises a kink-resistant polymer.

11. The intraluminal catheter of claim 1, wherein a cross section of the first material at a joint between the first material and the second material is different than cross sections of the first material proximal to the joint.

12. The intraluminal catheter of claim 1, wherein a cross section of the second material at a joint between the first material and the second material is different than cross sections of the second material distal to the joint.

* * * * *